US007863425B2

(12) United States Patent
Crystal et al.

(10) Patent No.: US 7,863,425 B2
(45) Date of Patent: Jan. 4, 2011

(54) COMPOSITIONS AND METHODS FOR INHIBITING *YERSINIA PESTIS* INFECTION

(75) Inventors: Ronald G Crystal, New York, NY (US); Julie L Boyer, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/238,129

(22) Filed: Sep. 25, 2008

(65) Prior Publication Data
US 2009/0104232 A1      Apr. 23, 2009

Related U.S. Application Data

(60) Provisional application No. 60/975,245, filed on Sep. 26, 2007.

(51) Int. Cl.
    *C07K 16/00*      (2006.01)
(52) U.S. Cl. ................................... 530/388.1; 435/340
(58) Field of Classification Search ....................... None
    See application file for complete search history.

(56) References Cited

PUBLICATIONS

Anderson et al., "Recombinant V Antigen Protects Mice against Pneumonic and Bubonic Plague Caused by F1-Capsule-Positive and -Negative Strains of *Yersinia pestis*," Infec. Immun., 64: 4580-4585 (1996).
Bennett et al., "Gene gun mediated vaccination is superior to manual delivery for immunization with DNA vaccines expressing protective antigens from *Yersinia pestis* or Venezuelan Equine Encephalitis virus," Vaccine, 18: 588-596 (1999).
Green et al., "The SCID/Beige mouse as a model to investigate protection against *Yersinia pestis*," FEMS Immunol. Med. Microbiol., 23: 107-113 (1999).
Hersh et al., "Modulation of gene expression after replication-deficient, recombinant adenovirus-mediated gene transfer by the product of a second adenovirus vector," Gene Ther., 2: 124-131 (1995).
Hill et al., "Regions of *Yersinia pestis* V Antigen That Contribute to Protection against Plague Identified by Passive and Active Immunization," Infect. Immun., 65(11): 4476-4482 (1997).
Ingelsby et al., "Plague as a Biological Weapon," JAMA, 283: 2281-2290 (2000).
Kilonzo et al., "A decade of plague epidemiology and control in the Western Usambara mountains, north-east Tanzania," Acta Tropica, 50: 323-329 (1992).
Leary et al., "Active Immunization with Recombinant V Antigen from *Yersinia pestis* Protects Mice against Plague," Infect. Immun., 63: 2854-2858 (1995).
Meyer, "Therapy of Plague," JAMA, 144: 982-985 (1950).
Motin et al., "Passive Immunity to *Yersiniae* Mediated by Anti-Recombinant V Antigen and Protein A-V Antigen Fusion Peptide," Infect. Immun., 62: 192-201 (1994).
Mwengee et al., "Treatment of Plague with Gentamicin or Doxycycline in a Randomized Clinical Trial in Tanzania," Clin. Infect. Dis., 42: 614-621 (2006).
Parkhill et al., "Genome sequence of *Yersinia pestis*, the causative agent of plague," Nature, 413 (6855): 523-527 (2001).
Perry et al., "*Yersinia pestis*—Etiologic Agent of Plague," Clin. Microbiol. Rev., 10: 35-66 (1997).
Pettersson et al., "The V-antigen of *Yersinia* is surface exposed before target cell contact and involved in virulence protein translocation," Mol. Microbiol., 32: 961-976 (1999).
Russell et al., "A comparison of Plague vaccine, USP and EV76 vaccine induced protection against *Yersinia pestis* in a murine model," Vaccine, 13: 1551-1556 (1995).
Sarker et al., "The *Yersinia* Yop Virulon: LcrV Is Required for Extrusion of the Translocators YopB and YopD," J. Bacteriol., 180: 1207-1214 (1998).
Smego et al., "*Yersiniosis* I: Microbiological and Clinicoepidemiological Aspects of Plague and Non-Plague *Yersinia* Infections," Eur. J. Clin. Microbial. Infect. Dis., 18: 1-15 (1999).
Sofer-Podesta et al., "Protection Against a Lethal *Yersinia pestis* Challenge by an Anti-V Antigen Monoclonal Antibody Delivered with an Adenovirus Gene Transfer Vector," Molecular Therapy, 16 (Suppl. 1): S268 (2008).
Titball et al., "*Yersinia pestis* (plague) vaccines," Expert Opin. Biol Ther., 4: 965-973 (2004).
Titball et al, "Vaccination against bubonic and pneumonic plague," Vaccine, 19: 4175-4184 (2001).
Titball et al, "Plague," in Plotkin et al., eds., Vaccine, WB Saunders, Philadelphia, p. 999 (2004).
Wagle, "Recent Advances in the Treatment of Bubonic Plague," Indian J. Med. Sci., 2: 489-494 (1948).
Wang et al., "A DNA vaccine producing LcrV antigen in oligomers is effective in protecting mice from lethal mucosal challenge of plague," Vaccine, 22: 3348-3357 (2004).
Williamson et al, "Co-immunisation with a plasmid DNA cocktail primes mice against anthrax and plague," Vaccine, 20: 2933-2941 (2002).
Boyer et al., Am. Soc. Gene Ther. 10th Annual Meeting, Abstract # 450970 (2007).
Chiuchiolo et al., Mol. Ther., 9, S215, Abstract # 570 (2004).
Chiuchiolo et al., Mol. Ther., 11, S27, Abstract # 67 (2005).
Chiuchiolo et al., Mol. Ther., 13, S423, Abstract # 605 (2006).
Sofer-Podesta et al., Am. Soc. Gene Ther. 10th Annual Meeting, Abstract # 450724 (2007).

*Primary Examiner*—Patrica A Duffy
(74) *Attorney, Agent, or Firm*—Leydig, Voit & Mayer, Ltd.

(57) ABSTRACT

The invention provides a gene transfer vector for inducing an immune response against *Yersinia pestis* in a mammal. The gene transfer vector comprises a nucleic acid sequence encoding an immunogenic portion of one or more proteins of *Yersinia pestis* and/or a nucleic acid sequence encoding a monoclonal antibody directed against *Yersinia pestis*. The invention further provides a method of producing an immune response against *Yersinia pestis* in a mammal comprising administration of the gene transfer vector to the mammal. The invention also provides a monoclonal antibody directed against the Virulence (V) antigen of *Y. pestis*, as well as a hybridoma cell line producing same and a nucleic acid sequence encoding same.

2 Claims, No Drawings

COMPOSITIONS AND METHODS FOR INHIBITING *YERSINIA PESTIS* INFECTION

CROSS-REFERENCE TO RELATED APPLICATIONS

This patent application claims the benefit of U.S. Provisional Patent Application No. 60/975,245, filed Sep. 26, 2007 which is incorporated by reference.

STATEMENT REGARDING FEDERALLY SPONSORED RESEARCH AND DEVELOPMENT

This invention was made with government support under grants AI055844 and AI057158 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,000 Byte ASCII (Text) file named "703522ST25.TXT," created on Sep. 25, 2008.

BACKGROUND OF THE INVENTION

*Yersinia pestis* is a gram-negative bacterium that is the etiological agent of plague, and is a potential bioterrorism agent. There are three forms of the human disease: bubonic, septicemic, and pneumonic (Perry et al., *Clin. Microbiol. Rev.*, 10: 35-66 (1997), and Ingelsby et al., *JAMA*, 283: 2281-2290 (2000)). Pneumonic plague is of most concern as a biological threat due to its rapid onset, high mortality, and rapid spread. While antibiotics can be used to treat plague, the fatality rate is high when treatment is delayed more than 24 hours after the onset of disease symptoms (Perry et al., supra, and Smego et al., *Eur. J. Clin. Microbiol. Infect. Dis.*, 18: 1-15 (1999)).

No vaccines against plague are currently available in the United States. Several vaccines have been developed, including killed whole-cell formulations and the live EV76 vaccine (Titball et al., in Plotkin et al., eds., *Vaccines*, WB Saunders, Philadelphia, p. 999 (2004), Russell et al., *Vaccine*, 13: 1551-1556 (1995), Titball et al., *Vaccine*, 19: 4175-4184 (2001), and Titball et al., *Expert Opin. Biol Ther.*, 4: 965-973 (2004)). While these vaccines have been tested in humans, they offer low levels of protection, have numerous side effects, and require frequent immunizations with consequent prolonged time to develop immunity.

Vaccines based on the virulence (V) antigen of *Y. pestis* also have been developed, including subunit and DNA vaccines. Immunization with a subunit vaccine against V antigen provides protection against plague in mice (Anderson et al., *Infec. Immun.*, 64: 4580-4585 (1996), Leary et al., *Infect. Immun.*, 63: 2854-2858 (1995), Green et al., *FEMS Immunol. Med. Microbiol.*, 23: 107-113 (1999), Motin et al., *Infect. Immun.*, 62: 192-201 (1994), Bennett et al., *Vaccine*, 18: 588-596 (1999), and Williamson et al., *Vaccine*, 20: 2933-2941 (2002)). DNA vaccines based on V antigen elicit low antibody titers, and protection against *Y. pestis* challenges is reached only after several immunizations (Wang et al., *Vaccine*, 22: 3348-3357 (2004)).

Accordingly, there remains a need for alternative compositions and methods for protection against *Y. pestis* infection that elicit a rapid and efficient immune response in a broad spectrum of the population. The invention provides such a composition and method. These and other advantages of the invention, as well as additional inventive features, will be apparent from the description of the invention provided herein.

BRIEF SUMMARY OF THE INVENTION

The invention provides a gene transfer vector comprising a nucleic acid sequence which encodes (a) an immunogenic portion of one or more proteins of *Yersinia pestis* and (b) a heterologous signal peptide, wherein the nucleic acid sequence comprises codons expressed more frequently in humans than in *Yersinia pestis*. The invention also provides a gene transfer vector comprising a nucleic acid sequence which encodes a monoclonal antibody directed against *Yersinia pestis*.

The invention also provides a gene transfer vector comprising (a) a nucleic acid sequence which encodes an immunogenic portion of one or more proteins of *Yersinia pestis* and a heterologous signal peptide, and (b) a nucleic acid sequence which encodes a monoclonal antibody directed against *Yersinia pestis*.

The invention further provides a method of producing an immune response against *Yersinia pestis* in a mammal. The method comprises administering to the mammal a gene transfer vector having a nucleic acid sequence which encodes (a) an immunogenic portion of one or more proteins of *Yersinia pestis* and (b) a heterologous signal peptide, wherein the nucleic acid sequence comprises codons expressed more frequently in humans than in *Yersinia pestis*, and wherein the nucleic acid sequence is expressed to produce the immunogenic portion of the one or more proteins in the mammal.

The invention provides another method of producing an immune response against *Yersinia pestis* in a mammal. The method comprises administering to the mammal a gene transfer vector comprising a nucleic acid sequence which encodes a monoclonal antibody directed against *Yersinia pestis*, and wherein the nucleic acid sequence is expressed to produce the monoclonal antibody in the mammal.

The invention provides a monoclonal antibody which comprises (a) a heavy chain directed against the virulence antigen of *Y. pestis* encoded by the nucleic acid sequence of SEQ ID NO: 4, and (b) a light chain directed against the virulence antigen of *Y. pestis* encoded by the nucleic acid sequence of SEQ ID NO: 5. Also provided by the invention is a hybridoma cell line that produces such a monoclonal antibody, as well as a nucleic acid sequence encoding a monoclonal antibody directed against the virulence antigen of *Y. pestis* comprising SEQ ID NO: 4 and SEQ ID NO: 5.

DETAILED DESCRIPTION OF THE INVENTION

The invention provides a gene transfer vector comprising a nucleic acid sequence which encodes at least an immunogenic portion of one or more proteins of *Yersinia pestis* and a heterologous signal peptide. The nucleic acid sequence comprises codons expressed more frequently in humans than in *Yersinia pestis*. The invention also provides a gene transfer vector comprising a nucleic acid sequence which encodes a monoclonal antibody directed against *Yersinia pestis*. The invention provides a gene transfer vector comprising (a) a nucleic acid sequence which encodes an immunogenic portion of one or more proteins of *Yersinia pestis* and a heterologous signal peptide, and (b) a nucleic acid sequence which encodes a monoclonal antibody directed against *Yersinia pes-* tis. The invention further provides a method of producing an immune response against *Yersinia pestis* in a mammal, which method comprises administering to the mammal the above-described gene transfer vector. In addition, the invention provides the aforementioned monoclonal antibody and nucleic acid sequence. Various aspects of the inventive gene transfer vector, monoclonal antibody, nucleic acid sequence, and method are discussed below. Although each parameter is discussed separately, the inventive gene transfer vector, monoclonal antibody, nucleic acid sequence, and method comprise combinations of the parameters set forth below to evoke protection against *Yersinia pestis* infection in a human. Accordingly, any combination of parameters can be used to characterize the inventive gene transfer vector, monoclonal antibody, nucleic acid sequence, and method.

A "gene transfer vector" is any molecule or composition that has the ability to carry a heterologous nucleic acid sequence encoding a protein into a suitable host cell where synthesis of the encoded protein takes place. Typically and preferably, a gene transfer vector is a nucleic acid molecule that has been engineered, using recombinant DNA techniques that are known in the art, to incorporate the heterologous nucleic acid sequence. Desirably, the gene transfer vector is comprised of DNA. Examples of suitable DNA-based gene transfer vectors include plasmids and viral vectors. However, gene transfer vectors that are not based on nucleic acids, such as liposomes, are also known and used in the art. The inventive gene transfer vector can be based on a single type of nucleic acid (e.g., a plasmid) or non-nucleic acid molecule (e.g., a lipid or a polymer). The inventive gene transfer vector can be integrated into the host cell genome, or can be present in the host cell in the form of an episome.

Preferably, the gene transfer vector is a viral vector. Suitable viral vectors include, for example, retroviral vectors, herpes simplex virus (HSV)-based vectors, parvovirus-based vectors, e.g., adeno-associated virus (AAV)-based vectors, AAV-adenoviral chimeric vectors, and adenovirus-based vectors. These viral vectors can be prepared using standard recombinant DNA techniques described in, for example, Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994).

In a preferred embodiment of the invention, the gene transfer vector is an adenoviral vector. While non-human adenovirus (e.g., simian, avian, canine, ovine, or bovine adenoviruses) can be used to generate the adenoviral vector, a human adenovirus preferably is used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). Preferably, in the context of the invention, the adenoviral vector is of human subgroup C, especially serotype 2 or even more desirably serotype 5. However, non-group C adenoviruses can be used to prepare adenoviral gene transfer vectors for delivery of gene products to host cells. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Application Publications WO 97/12986 and WO 98/53087.

The adenoviral vector desirably is replication-deficient. By "replication-deficient" is meant that the adenoviral vector requires complementation of one or more regions of the adenoviral genome that are required for replication, as a result of, for example, a deficiency in at least one replication-essential gene function (i.e., such that the adenoviral vector does not replicate in typical host cells, especially those in a human patient that could be infected by the adenoviral vector in the course of the inventive method). A deficiency in a gene, gene function, gene, or genomic region, as used herein, is defined as a mutation or deletion of sufficient genetic material of the viral genome to obliterate or impair the function of the gene (e.g., such that the function of the gene product is reduced by at least about 2-fold, 5-fold, 10-fold, 20-fold, 30-fold, or 50-fold) whose nucleic acid sequence was mutated or deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2).

The adenoviral vector desirably requires complementation of, at most, the E1, E2A, and E4 regions of the adenoviral genome for propagation. Thus, for propagation, the adenoviral vector can require complementation of, at most, (a) the E1 region, (b) the E2A region, (c) the E4 region, (d) the E1 and E2A regions, (e) the E1 and E4 regions, (f) the E2A and E4 regions, or (g) the E1, E2A, and E4 regions. Preferably, the adenoviral vector requires complementation of, at most, the E1 and/or E4 regions of the adenoviral genome for propagation.

The adenoviral vector can contain deletions and/or mutations in portions of the adenoviral genome other than the E1, E2A, and/or E4 regions. For example, the adenoviral vector also can have deletions and/or mutations in the major late promoter (MLP), as discussed in International Patent Application Publication WO 00/00628, in the E3 region (e.g., an Xba I deletion of the E3 region), which does not include replication-essential gene functions, and/or in regions that include replication-essential gene functions but so as not to require complementation of regions other than E1, E2A, and/or E4 for propagation.

With respect to the E1 region, the adenoviral vector can lack all or a portion of the E1A region and/or all or a portion of the E1B region, e.g., lack at least one replication-essential gene function of each of the E1A and E1B regions, thus requiring complementation of the E1A region and the E1B region of the adenoviral genome for replication.

With respect to the E2A region, the adenoviral vector preferably does not comprise a complete deletion of the E2A region, which deletion preferably is less than about 230 base pairs in length. Generally, the E2A region of the adenovirus codes for a DBP (DNA binding protein), which is a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology,* 196: 269-281 (1993)). While deletions in the E2A region coding for the Ct region of the DBP have no effect on viral replication, deletions in the E2A region which code for amino acids 2 to 38 of the Nt domain of the DBP impair viral replication. It is preferable that the adenoviral vector contains this portion of the E2A region of the adenoviral genome. In particular, for example, the desired portion of the E2A region to be retained is that portion of the E2A region of the adenoviral genome which is defined by the 5' end of the E2A region. This portion of the adenoviral genome desirably is included in the adenoviral vector because it is not complemented in current E2A complementing cell lines so as to provide the desired level of viral propagation.

With respect to the E4 region, the adenoviral vector can lack all or a portion of the E4 region. Desirably, the adenoviral vector contains a deletion or mutation of Open Reading Frame (ORF) 6 of the E4 region, which is believed to be the only portion of the E4 region required for propagation of the adenoviral vector.

In one embodiment of the invention, the adenoviral vector comprises an adenoviral genome that lacks all or a portion of each of the E1 and E4 regions (i.e., the adenoviral vector is an E1/E4-deficient adenovirus), preferably with the entire coding region of the E4 region having been deleted from the adenoviral genome. In other words, all the open reading frames (ORFs) of the E4 region have been removed. In another embodiment, the adenoviral vector is rendered replication-deficient by deletion of all of the E1 region and by deletion of a portion of the E4 region. The E4 region of the adenoviral vector can retain the native E4 promoter, polyadenylation sequence, and/or the right-side inverted terminal repeat (ITR).

In some embodiments, the adenoviral vector which requires complementation of, for example, one or more gene functions of the E1 region and one or more gene functions of the E4 region can include a spacer sequence to provide viral growth in a complementing cell line similar to that achieved by an adenoviral vector which requires complementation of one or more gene functions of only the E1 region. The spacer sequence can contain any nucleotide sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer element sequence can be coding or non-coding, and native or non-native with respect to the adenoviral genome, but does not restore the replication-essential function to the deficient region. The spacer element can be located in any region of the adenoviral vector, but preferably the spacer is located in the E4 region of the adenoviral genome. The use of a spacer in an adenoviral vector is described in U.S. Pat. No. 5,851,806.

While the adenoviral vector preferably requires complementation of, at most, replication-essential gene functions of the E1 and/or E4 regions of the adenoviral genome for replication (i.e., propagation), it is possible for the adenoviral vector to have other deficiencies such that other complementation is required for propagation. In particular, the adenoviral genome can be modified to disrupt one or more replication-essential gene functions as desired by the practitioner, so long as the adenoviral vector remains replication-deficient and can be propagated using, for example, complementing cells and/or exogenous DNA (e.g., helper adenovirus) encoding the disrupted replication-essential gene functions. In this respect, the adenoviral vector can be deficient in replication-essential gene functions of only the early regions of the adenoviral genome, only the late regions of the adenoviral genome, both the early and late regions of the adenoviral genome, or all adenoviral genes (i.e., a high capacity adenovector (HC-Ad), see Morsy et al., *Proc. Natl. Acad. Sci. USA,* 95: 7876-7871 (1998), Chen et al., *Proc. Natl. Acad. Sci. USA,* 94: 1645-1650 (1997), and Kochanek et al., *Hum. Gene Ther.,* 10: 2451-2459 (1999)). Adenoviral vectors and methods for their construction are well known in the art and are described in, for example, U.S. Pat. Nos. 5,559,099, 5,712,136, 5,731,190, 5,837,511, 5,846,782, 5,849,561, 5,851,806, 5,962,311, 5,965,358, 5,965,541, 5,981,225, 5,994,106, 6,020,191, 6,083,716, 6,113,913, 6,127,175, 6,168,941, 6,225,289, 6,383,795, 6,482,616, 6,514,943, 7,141,406, and 7,195,896, U.S. Patent Application Publication Nos. 2001/0043922 A1, 2002/0004040 A1, 2002/0110545 A1, and 2004/0161848 A1, International Patent Applications 94/28152, WO 95/02697, WO 95/16772, WO 95/34671, WO 96/22378, WO 97/12986, WO 97/21826, WO 00/00628, and WO 03/022311, and Thomas Shenk, "Adenoviridae and their Replication," and M. S. Horwitz, "Adenoviruses," Chapters 67 and 68, respectively, in *Virology,* B. N. Fields et al., eds., 3d ed., Raven Press, Ltd., New York (1996). Moreover, numerous adenoviral vectors are available commercially. The production of adenoviral gene transfer vectors involves using standard molecular biological techniques such as those described in, for example, Sambrook et al., supra, Ausubel et al., supra, and several of the other references mentioned herein.

The adenoviral vector typically will be produced in a complementing cell line that provides gene functions not present in the adenoviral vector, but required for viral propagation, at appropriate levels in order to generate high titers of adenoviral vector stock. Desirably, the complementing cell line comprises, integrated into the cellular genome, adenoviral nucleic acid sequences which encode gene functions required for adenoviral propagation. A preferred cell line complements for at least one and preferably all replication-essential gene functions not present in a replication-deficient adenoviral vector. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the adenoviral genome recombining with the cellular DNA. Accordingly, the presence of replication competent adenoviruses (RCA) is minimized if not avoided in the adenoviral vector stock, which, therefore, is suitable for certain therapeutic purposes, especially vaccination purposes. The lack of RCA in the adenoviral vector stock avoids the replication of the adenoviral vector in non-complementing cells. Construction of such a complementing cell lines involve standard molecular biology and cell culture techniques, such as those described in Sambrook et al., supra, and Ausubel et al., supra.

Complementing cell lines for producing the adenoviral vector include, but are not limited to, 293 cells (described in, e.g., Graham et al., *J. Gen. Virol.*, 36, 59-72 (1977)), PER.C6 cells (described in, e.g., International Patent Application Publication WO 97/00326, and U.S. Pat. Nos. 5,994,128 and 6,033,908), and 293-ORF6 cells (described in, e.g., International Patent Application Publication WO 95/34671, U.S. Pat. No. 7,195,896, and Brough et al., *J. Virol.*, 71: 9206-9213 (1997)). Additional complementing cells are described in, for example, U.S. Pat. Nos. 6,677,156 and 6,682,929, and International Patent Application Publication WO 03/20879. In some instances, the cellular genome need not comprise nucleic acid sequences, the gene products of which complement for all of the deficiencies of the adenoviral vector. One or more replication-essential gene functions lacking in the adenoviral vector can be supplied by a helper virus, e.g., an adenoviral vector that supplies in trans one or more essential gene functions required for replication of the desired adenoviral vector. Helper virus is often engineered to prevent packaging of infectious helper virus. For example, one or more replication-essential gene functions of the E1 region of the adenoviral genome are provided by the complementing cell, while one or more replication-essential gene functions of the E4 region of the adenoviral genome are provided by a helper virus.

In addition to modification (e.g., deletion, mutation, or replacement) of adenoviral sequences encoding replication-essential gene functions, the adenoviral genome can contain benign or non-lethal modifications, i.e., modifications which do not render the adenovirus replication-deficient, or, desirably, do not adversely affect viral functioning and/or production of viral proteins, even if such modifications are in regions of the adenoviral genome that otherwise contain replication-essential gene functions. Such modifications commonly result from DNA manipulation or serve to facilitate construction of the adenoviral vector. For example, it can be advantageous to remove or introduce restriction enzyme sites in the adenoviral genome. Such benign mutations often have no detectable adverse effect on viral functioning.

Similarly, the coat protein of the adenoviral vector can be manipulated to alter the binding specificity or recognition of the adenovirus for a receptor on a potential host cell. For adenovirus, such manipulations can include deletion of regions of adenovirus coat proteins (e.g., fiber, penton, or hexon), insertions of various native or non-native ligands into portions of a coat protein, and the like. Manipulation of the coat protein can broaden the range of cells infected by the adenoviral vector or enable targeting of the adenoviral vector to a specific cell type.

Any suitable technique for altering native binding to a host cell, such as native binding of the fiber protein to its cellular receptor (e.g., a coxsackievirus and adenovirus receptor (CAR)), can be employed. For example, differing fiber lengths can be exploited to ablate native binding to cells. In an alternative embodiment, the adenoviral fiber protein can be modified to reduce the number of amino acids in the fiber shaft, thereby creating a "short-shafted" fiber (as described in, for example, U.S. Pat. No. 5,962,311). Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenoviral vector comprising a short-shafted fiber enables targeting of the adenovirus to a desired cell-surface receptor by the introduction of a normative amino acid sequence either into the penton base or the fiber knob.

In yet another embodiment, the nucleic acid residues encoding amino acid residues associated with native substrate binding can be changed, supplemented, or deleted (see, e.g., International Patent Application Publication WO 00/15823, Einfeld et al., *J. Virol.*, 75(23): 11284-11291 (2001), and van Beusechem et al., *J. Virol.*, 76(6): 2753-2762 (2002)) such that the adenoviral vector incorporating the mutated nucleic acid residues (or having the fiber protein encoded thereby) is less able to bind its native substrate. For example, the native CAR and integrin binding sites of the adenoviral vector, such as the knob domain of the adenoviral fiber protein and an Arg-Gly-Asp (RGD) sequence located in the adenoviral penton base, respectively, can be removed or disrupted.

Any suitable amino acid residue(s) of a fiber protein that mediates or assists in the interaction between the knob and the native cellular receptor can be mutated or removed, so long as the fiber protein is able to trimerize. Similarly, amino acids can be added to the fiber knob as long as the fiber protein retains the ability to trimerize. Suitable residues include amino acids within the exposed loops of the fiber knob domain, such as, for example, the AB loop, the DE loop, the FG loop, and the HI loop.

Any suitable amino acid residue(s) of a penton base protein that mediates or assists in the interaction between the penton base and integrins can be mutated or removed. Suitable residues include, for example, one or more of the five RGD amino acid sequence motifs located in the hypervariable region of the Ad5 penton base protein (as described, for example, in U.S. Pat. No. 5,731,190). The native integrin binding sites on the penton base protein also can be disrupted by modifying the nucleic acid sequence encoding the native RGD motif such that the native RGD amino acid sequence is conformationally inaccessible for binding to an integrin receptor, such as by inserting a DNA sequence into or adjacent to the nucleic acid sequence encoding the adenoviral penton base protein.

The adenoviral vector can comprise a fiber protein and a penton base protein that do not bind to their respective native cellular binding sites (e.g., CAR and integrins). Alternatively, the adenoviral vector comprises a fiber protein and a penton base protein that bind to their respective native cellular binding sites, but with less affinity than the corresponding wild-type coat proteins. The adenoviral vector exhibits reduced binding to native cellular binding sites if a modified adenoviral fiber protein and penton base protein binds to their respective native cellular binding sites with at least about 5-fold, 10-fold, 20-fold, 30-fold, 50-fold, or 100-fold less affinity than a non-modified adenoviral fiber protein and penton base protein of the same serotype.

The adenoviral vector also can comprise a chimeric coat protein comprising a non-native amino acid sequence that binds a substrate (i.e., a ligand), such as a cellular receptor other than a native cellular receptor (e.g., CAR or the αv integrin receptor). The non-native amino acid sequence of the chimeric adenoviral coat protein allows the adenoviral vector comprising the chimeric coat protein to bind and, desirably, infect host cells not naturally infected by a corresponding adenovirus without the non-native amino acid sequence (i.e., host cells not infected by the corresponding wild-type adenovirus), to bind to host cells naturally infected by the corresponding wild-type adenovirus with greater affinity than the corresponding adenovirus without the non-native amino acid sequence, or to bind to particular target cells with greater affinity than non-target cells. A "non-native" amino acid sequence can comprise an amino acid sequence not naturally present in the adenoviral coat protein or an amino acid sequence found in the adenoviral coat but located in a non-native position within the capsid. By "preferentially binds" is meant that the non-native amino acid sequence binds a receptor, such as, for instance, αvβ3 integrin, with at least about 3-fold greater affinity (e.g., at least about 5-fold, 10-fold, 15-fold, 20-fold, 25-fold, 35-fold, 45-fold, or 50-fold greater affinity) than the non-native ligand binds a different receptor, such as, for instance, αvβ1 integrin.

The adenoviral vector can comprise a chimeric coat protein comprising a non-native amino acid sequence that confers to the chimeric coat protein the ability to bind to an immune cell more efficiently than a wild-type adenoviral coat protein. In particular, the adenoviral vector can comprise a chimeric adenoviral fiber protein comprising a non-native amino acid sequence which facilitates uptake of the adenoviral vector by immune cells, preferably antigen presenting cells, such as dendritic cells, monocytes, and macrophages. In a preferred embodiment, the adenoviral vector comprises a chimeric fiber protein comprising an amino acid sequence (e.g., a non-native amino acid sequence) comprising an RGD motif including, but not limited to, CRGDC (SEQ ID NO: 1), CXCRGDCXC (SEQ ID NO: 2), wherein X represents any amino acid, and CDCRGDCFC (SEQ ID NO: 3), which increases transduction efficiency of the adenoviral vector into dendritic cells. The RGD-motif, or any non-native amino acid sequence, preferably is inserted into the adenoviral fiber knob region, ideally in an exposed loop of the adenoviral knob, such as the HI loop. A non-native amino acid sequence also can be appended to the C-terminus of the adenoviral fiber protein, optionally via a spacer sequence. The spacer sequence preferably comprises between one and two-hundred amino acids, and can (but need not) have an intended function.

The non-native amino acid sequence can optionally recognize a protein typically found on dendritic cell surfaces such as adhesion proteins, chemokine receptors, complement receptors, co-stimulation proteins, cytokine receptors, high level antigen presenting molecules, homing proteins, marker proteins, receptors for antigen uptake, signaling proteins, virus receptors, etc. Examples of such potential ligand-binding sites in dendritic cells include αvβ3 integrins, αvβ5 integrins, 2A1, 7-TM receptors, CD1, CD11a, CD11b, CD11c, CD21, CD24, CD32, CD4, CD40, CD44 variants, CD46, CD49d, CD50, CD54, CD58, CD64, ASGPR, CD80, CD83, CD86, E-cadherin, integrins, M342, MHC-I, MHC-II, MIDC-8, MMR, OX62, p200-MR6, p55, S100, TNF-R, etc.

Where dendritic cells are targeted, the non-native amino acid sequence preferably recognizes the CD40 cell surface protein, such as, for example, by way of a CD-40 (bi)specific antibody fragment or by way of a domain derived from the CD40L polypeptide.

The non-native amino acid sequence optionally can recognize a protein typically found on macrophage cell surfaces, such as phosphatidylserine receptors, vitronectin receptors, integrins, adhesion receptors, receptors involved in signal transduction and/or inflammation, markers, receptors for induction of cytokines, or receptors up-regulated upon challenge by pathogens, members of the group B scavenger receptor cysteine-rich (SRCR) superfamily, sialic acid binding receptors, members of the Fc receptor family, B7-1 and B7-2 surface molecules, lymphocyte receptors, leukocyte receptors, antigen presenting molecules, and the like. Examples of suitable macrophage surface target proteins include, but are not limited to, heparin sulfate proteoglycans, αvβ3 integrins, αvβ5 integrins, B7-1, B7-2, CD11c, CD13, CD16, CD163, CD1a, CD22, CD23, CD29, Cd32, CD33, CD36, CD44, CD45, CD49e, CD52, CD53, CD54, CD71, CD87, CD9, CD98, Ig receptors, Fc receptor proteins (e.g., subtypes of Fcα, Fcγ, Fcε, etc.), folate receptor b, HLA Class I, Sialoadhesin, siglec-5, and the toll-like receptor-2 (TLR2).

The non-native amino acid sequence can recognize a protein typically found on B-cell surfaces, such as integrins and other adhesion molecules, complement receptors, interleukin receptors, phagocyte receptors, immunoglobulin receptors, activation markers, transferrin receptors, members of the scavenger receptor cysteine-rich (SRCR) superfamily, growth factor receptors, selectins, MHC molecules, TNF-receptors, and TNF-R associated factors. Examples of typical B-cell surface proteins include β-glycan, B cell antigen receptor (BAC), B7-2, B-cell receptor (BCR), C3d receptor, CD1, CD18, CD19, CD20, CD21, CD22, CD23, CD35, CD40, CD5, CD6, CD69, CD69, CD71, CD79a/CD79b dimer, CD95, endoglin, Fas antigen, human Ig receptors, Fc receptor proteins (e.g., subtypes of Fca, Fcg, Fcε, etc.), IgM, gp200-MR6, Growth Hormone Receptor (GH-R), ICAM-1, ILT2, CD85, MHC class I and II molecules, transforming growth factor receptor (TGF-R), α4β7 integrin, and αvβ3 integrin.

In another embodiment, the adenoviral vector can comprise a chimeric virus coat protein that is not selective for a specific type of eukaryotic cell. The chimeric coat protein differs from a wild-type coat protein by an insertion of a non native amino acid sequence into or in place of an internal coat protein sequence, or attachment of a non-native amino acid sequence to the N- or C-terminus of the coat protein. For example, a ligand comprising about five to about nine lysine residues (preferably seven lysine residues) is attached to the C-terminus of the adenoviral fiber protein via a non-functional spacer sequence. In this embodiment, the chimeric virus coat protein efficiently binds to a broader range of eukaryotic cells than a wild-type virus coat, such as described in U.S. Pat. No. 6,465,253 and International Patent Application Publication WO 97/20051.

The ability of the adenoviral vector to recognize a potential host cell can be modulated without genetic manipulation of the coat protein, i.e., through use of a bi-specific molecule. For instance, complexing an adenovirus with a bispecific molecule comprising a penton base-binding domain and a domain that selectively binds a particular cell surface binding site enables the targeting of the adenoviral vector to a particular cell type. Likewise, an antigen can be conjugated to the surface of the adenoviral particle through non-genetic means.

A non-native amino acid sequence can be conjugated to any of the adenoviral coat proteins to form a chimeric adenoviral coat protein. Therefore, for example, a non-native amino acid sequence can be conjugated to, inserted into, or attached to a fiber protein, a penton base protein, a hexon protein, proteins IX, VI, or IIIa, etc. Methods for employing such proteins are well known in the art (see, e.g., U.S. Pat. Nos. 5,543,328; 5,559,099; 5,712,136; 5,731,190; 5,756,086; 5,770,442; 5,846,782; 5,962,311; 5,965,541; 5,846,782; 6,057,155; 6,127,525; 6,153,435; 6,329,190; 6,455,314; 6,465,253; 6,576,456; 6,649,407; 6,740,525, 6,951,755, and International Patent Application Publications WO 96/07734, WO 96/26281, WO 97/20051, WO 98/07877, WO 98/07865, WO 98/40509, WO 98/54346, WO 00/15823, WO 01/58940, and WO 01/92549). The chimeric adenoviral coat protein can be generated using standard recombinant DNA techniques known in the art. Preferably, the nucleic acid sequence encoding the chimeric adenoviral coat protein is located within the adenoviral genome and is operably linked to a promoter that regulates expression of the coat protein in a wild-type adenovirus. Alternatively, the nucleic acid sequence encoding the chimeric adenoviral coat protein is located within the adenoviral genome and is part of an expression cassette which comprises genetic elements required for efficient expression of the chimeric coat protein.

The coat protein portion of the chimeric adenovirus coat protein can be a full-length adenoviral coat protein to which the non-native amino acid sequence is appended, or it can be truncated, e.g., internally or at the C- and/or N-terminus. However modified (including the presence of the non-native amino acid), the chimeric coat protein preferably is able to incorporate into an adenoviral capsid. Where the non-native amino acid sequence is attached to the fiber protein, preferably it does not disturb the interaction between viral proteins or fiber monomers. Thus, the non-native amino acid sequence preferably is not itself an oligomerization domain, as such can adversely interact with the trimerization domain of the adenovirus fiber. Preferably the non-native amino acid sequence is added to the virion protein, and is incorporated in such a manner as to be readily exposed to a substrate, cell surface-receptor, or immune cell (e.g., at the N- or C-terminus of the adenoviral protein, attached to a residue facing a substrate, positioned on a peptide spacer, etc.) to maximally expose the non-native amino acid sequence. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate, cell surface receptor, or immune cell. Where the non-native amino acid sequence is attached to the hexon, preferably it is within a hypervariable region (Crawford-Miksza et al., *J. Virol.*, 70(3): 1836-44 (1996)). Where the non-native amino acid is attached to or replaces a portion of pIX, preferably it is within the C-terminus of pIX. Use of a spacer sequence to extend the non-native amino acid sequence away from the surface of the adenoviral particle can be advantageous in that the non-native amino acid sequence can be more available for binding to a receptor, and any steric interactions between the non-native amino acid sequence and the adenoviral fiber monomers can be reduced.

Binding affinity of a non-native amino acid sequence to a cellular receptor can be determined by any suitable assay, a variety of which assays are known and are useful in selecting a non-native amino acid sequence for incorporating into an adenoviral coat protein. Desirably, the transduction levels of host cells are utilized in determining relative binding efficiency. Thus, for example, host cells displaying αvβ3 integrin on the cell surface (e.g., MDAMB435 cells) can be exposed to an adenoviral vector comprising the chimeric coat protein and the corresponding adenovirus without the non-native amino acid sequence, and then transduction efficiencies can be compared to determine relative binding affinity. Similarly, both host cells displaying αvβ3 integrin on the cell surface (e.g., MDAMB435 cells) and host cells displaying predominantly αvβ1 on the cell surface (e.g., 293 cells) can be exposed to the adenoviral vector comprising the chimeric coat protein, and then transduction efficiencies can be compared to determine binding affinity.

In other embodiments (e.g., to facilitate purification or propagation within a specific engineered cell type), a non-native amino acid (e.g., ligand) can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J. Cell. Biol.*, 130: 1189 (1995)). A ligand can even bind non-peptide substrates, such as plastic (e.g., Adey et al., *Gene*, 156: 27 (1995)), biotin (Saggio et al., *Biochem. J*, 293: 613 (1993)), a DNA sequence (Cheng et al., *Gene*, 171: 1 (1996), and Krook et al., *Biochem. Biophys., Res. Commun.*, 204: 849 (1994)), streptavidin (Geibel et al., *Biochemistry*, 34: 15430 (1995), and Katz, *Biochemistry*, 34: 15421 (1995)), nitrostreptavidin (Balass et al., *Anal. Biochem.*, 243: 264 (1996)), heparin (Wickham et al., *Nature Biotechnol.*, 14: 1570-73 (1996)), and other substrates.

Modifications to adenoviruses are described in U.S. Pat. Nos. 5,543,328, 5,559,099, 5,712,136, 5,731,190, 5,756,086, 5,770,442, 5,846,782, 5,871,727, 5,885,808, 5,922,315, 5,962,311, 5,965,541, 6,057,155, 6,127,525, 6,153,435, 6,329,190, 6,455,314, 6,465,253, 6,576,456, 6,649,407, 6,740,525, 6,951,755, and 7,195,896, U.S. Patent Application Publication 2003/0099619 A1, and International Patent Applications WO 96/07734, WO 96/26281, WO 97/20051, WO 98/07865, WO 98/07877, WO 98/40509, WO 98/54346, WO 00/15823, WO 01/58940, and WO 01/92549.

The inventive gene transfer vector comprises a nucleic acid sequence which encodes at least an immunogenic portion of one or more proteins of *Yersinia pestis* (i.e., one or more nucleic acid sequences encoding one or more immunogenic portions of one or more proteins) and a heterologous signal peptide. In another embodiment, the gene transfer vector comprises a nucleic acid sequence which encodes a monoclonal antibody directed against *Y. pestis*. The gene transfer vector comprises at least one nucleic acid sequence as described herein, i.e., the gene transfer vector can comprise one nucleic acid sequence as described herein or more than one nucleic acid sequence as described herein (i.e., two or more nucleic acid sequences). The nucleic acid sequence can be obtained from any source, e.g., isolated from nature, synthetically generated, isolated from a genetically engineered organism, and the like. An ordinarily skilled artisan will appreciate that any type of nucleic acid sequence (e.g., DNA, RNA, and cDNA) that can be inserted into a gene transfer vector can be used in connection with the invention. The nucleic acid sequence can be recombinantly produced, or can be a genomic nucleic acid sequence. Typically and preferably, the nucleic acid sequence is transcribed and translated into a peptide, polypeptide, or protein. For example, the nucleic acid sequence can be operatively linked to a suitable promoter, e.g., a constitutive or inducible promoter. In some cases, however, the nucleic acid sequence is not translated, such as when the nucleic acid sequence encodes an antisense molecule or a ribozyme.

When the gene transfer vector is a replication-deficient adenovirus, in one embodiment the nucleic acid sequence encoding the protein is preferably located in the E1 region of the adenoviral genome. However, when the gene transfer vector is deficient in the E1 region and the E4 region of the adenoviral genome, the nucleic acid sequence can be located in the E1 region or the E4 region of the adenoviral genome. In addition, when the gene transfer vector is deficient in the E3 region (e.g., in combination with a deficiency in the E1 and/or E4 regions), the nucleic acid sequence can be located in the E3 region of the adenoviral genome. The insertion of a nucleic acid sequence into the adenoviral genome (e.g., the E1 region of the adenoviral genome) can be facilitated by known methods, for example, by the introduction of a unique restriction site at a given position of the adenoviral genome.

Whatever type of nucleic acid sequence is used, the nucleic acid sequence preferably encodes an immunogenic portion of one or more proteins of Yersinia pestis. By "immunogenic portion" is meant any peptide, polypeptide, or portion thereof, that elicits an immune response (e.g., humoral and/or cell-mediated) against the organism from which it is obtained or derived from when introduced into a host. Assessing the immunogenicity of a protein, or portion thereof, can be determined using routine immunology techniques that are known in the art. With respect to humoral (i.e., antibody, immunoglobulin, or B cell) immune responses, for example, a suitable laboratory animal (e.g., a rabbit or mouse) can be immunized with a nucleic acid sequence encoding a candidate immunogenic portion of a Y. pestis protein. Serum levels of antibodies specific for the polypeptide, protein, or protein portion encoded by the nucleic acid sequence can be detected and measured using any suitable method, including radioimmunoassay (RIA) and enzyme-linked immunosorbent assay (ELISA) (see, e.g., Abbas et al., eds., Cellular and Molecular Immunology, 4th ed., W.B. Saunders Company, Philadelphia (2000)). The cell-mediated (i.e., T cell) immune response elicited by expression of a nucleic acid sequence encoding a candidate immunogenic Y. pestis protein can be assessed using, for example, the enzyme-linked immunospot (ELISPOT) assay. The ELISPOT assay enables detection of cells stimulated (e.g., by antigen) to produce cytokines. Preferably, the source cells for ELISPOT are isolated from the spleen and/or lymph nodes of immunized animals. The absence of a humoral or cell-mediated response to the polypeptide, protein, or protein portion encoded by the nucleic acid sequence indicates that the nucleic acid sequence does not encode an immunogenic portion of a Y. pestis protein. These methods, however, are merely exemplary. Indeed, any method for determining the immunogenicity of a candidate exotoxin or portion thereof is within the scope of the invention.

Yersinia pestis is a gram-negative, non-motile, non-spore-forming coccobacillus. Although Y. pestis does not have a true capsule, the F1 antigen forms a protein-carbohydrate envelope around the organism. Y. pestis replicates intracellularly during the early stages of infection and grows predominantly extracellularly at later stages of the infectious cycle. Virulence determinants required for intracellular as well as extracellular growth are essential for survival. Yersinia pestis has a circular genome of 4.65 megabases (MB), and contains three plasmids, the gene products of which affect virulence of the pathogen. The pYV plasmid (also referred to as the pCD1 plasmid or the low calcium response plasmid) encodes the Yersinia outer membrane proteins (Yops), the Yersinia secretion proteins (Ysc), and the Virulence (V) antigen. The pPst (or pPCP1) plasmid encodes the outer membrane protein plasminogen activator (Pla), while the pFra (or pMT1) plasmid encodes the genes for capsular protein (also known as Fraction 1) and a murine toxin. The sequence of the Yersinia pestis genome is disclosed in Parkhill et al., Nature, 413 (6855): 523-527 (2001). Although numerous virulence factors contribute to Y. pestis survival, the V antigen and the F1 capsular protein are the most relevant in evoking protective immunity.

Preferably, the nucleic acid sequence encodes an immunogenic portion of the virulence (V) antigen. The V antigen is a 37-kDa multifunctional protein, which participates in the type III secretion system in Y. pestis. In particular, the Y. pestis virulence (V) antigen is a protein that mediates the function of the Yersinia outer protein virulence factors (Yops) by facilitating the translocation of Yops with anti-host activity into the host cell. V antigen also exerts immunomodulatory effects in host defense mechanisms, inhibiting the pro-inflammatory response in the host by downregulation of IFN-γ and TNF-α and by up-regulation of the anti-inflammatory cytokine IL-10 in macrophages (see, e.g., Pettersson et al., Mol. Microbiol., 32: 961-976 (1999), and Sarker et al., J. Bacteriol., 180: 1207-1214 (1998)). While the nucleic acid sequence of the inventive gene transfer vector preferably is an immunogenic portion of the V antigen, nucleic acid sequences encoding immunogenic portions of other Yersina pestis proteins are also within the scope of the invention.

In one embodiment of the invention, the nucleic acid sequence preferably encodes a wild-type immunogenic portion of a Y. pestis protein. Alternatively, however, when expression of a wild-type Y. pestis protein is pathogenic in a host, the nucleic acid encodes a mutant form of the protein that is immunogenic, but not pathogenic, in a host. A mutant protein is preferably produced by introducing one or more mutations (e.g., point mutations, deletions, insertions, etc.) into the nucleic acid sequence encoding a naturally occurring protein. Such mutations are introduced in the nucleic acid sequence to effect one or more amino acid substitutions in an encoded protein. Thus, where mutations are introduced in the nucleic acid sequence encoding the protein, such mutations desirably will effect a substitution in the encoded protein whereby codons encoding positively charged residues (H, K, and R) are substituted with codons encoding positively charged residues, codons encoding negatively charged residues (D and E) are substituted with codons encoding negatively charged residues, codons encoding neutral polar residues (C, G, N, Q, S, T, and Y) are substituted with codons encoding neutral polar residues, and codons encoding neutral non polar residues (A, F, I, L, M, P, V, and W) are substituted with codons encoding neutral non polar residues. In addition, the nucleic acid sequence can encode a homolog of an immunogenic portion of a wild-type or mutant Y. pestis. A homolog of an immunogenic portion of a Y. pestis protein, whether wild-type or mutant, can be any peptide, polypeptide, or portion thereof, that is more than about 70% identical (preferably more than about 80% identical, more preferably more than about 90% identical, and most preferably more than about 95% identical, or even more than about 98% identical) to the immunogenic portion of the protein at the amino acid level. The degree of amino acid identity can be determined using any method known in the art, such as the BLAST sequence database.

In another embodiment, the gene transfer vector comprises a nucleic acid sequence which encodes a monoclonal antibody directed against Yersinia pestis. A "monoclonal" antibody refers to a homogenous population of antibody molecules that is specific to a particular antigen. The monoclonal antibody can be obtained or derived from any mammal, including a mouse, rat, or human. Monoclonal antibodies are typically produced by a single clone of B lymphocytes ("B cells"). Monoclonal antibodies are comprised of two heavy chains and two light chains, and the light chains can be classified as a kappa (κ) or lambda (λ) chain. Each heavy and light chain has two regions: a constant domain and a variable domain. The constant domain is identical in all antibodies of the same isotype. The variable domain differs between antibodies produced by different B cells. The nucleic acid sequence of the inventive gene transfer vector can encode both the heavy and light chains of a monoclonal antibody directed against *Y. pestis*, heavy or light chains of a monoclonal antibody directed against *Y. pestis*, or any active fragment of a monoclonal antibody directed against *Y. pestis*. Active fragments of a monoclonal antibody include any fragment that has at least one antigen binding site and can recognize and bind to at least one antigen of *Y. pestis*. Examples of active fragments of a monoclonal antibody include Fab fragments, F(ab')2 fragments, single-chain variable region (sFv) antibody fragments, and disulfide-stabilized variable region fragments (dsFv) (see, e.g., Janeway et al., supra, and Reiter et al., *Protein Engineering*, 7: 697-704 (1994)). Antibody-antigen binding can be assayed using any suitable method known in the art, such as, for example, radioimmunoassay (RIA), ELISA, Western blot, immunoprecipitation, and competitive inhibition assays (see, e.g., C. A. Janeway et al. (eds.), *Immunobiology*, 5$^{th}$ Ed., Garland Publishing, New York, N.Y. (2001), and U.S. Patent Application Publication No. 2002/0197266 A1). The monoclonal antibody encoded by the nucleic acid sequence comprises at least one variable domain, but can comprise more than one variable domain. The constant domain of the monoclonal antibody can be of any known isotype (e.g., IgM, IgG, IgA, IgE, or IgD).

The monoclonal antibody can be directed against any *Yersinia pestis* protein, such as those described above. Preferably, the monoclonal antibody is directed against the virulence (V) antigen of *Y. pestis*. In a preferred embodiment, the nucleic acid sequence encodes both the heavy and light chains of a monoclonal antibody directed against the V antigen of *Y. pestis*. A particularly preferred nucleic acid sequence encoding a heavy chain of a monoclonal antibody directed against the *Y. pestis* V antigen is set forth in SEQ ID NO: 4. A particularly preferred nucleic acid sequence encoding a light chain of a monoclonal antibody directed against the *Y. pestis* V antigen is set forth in SEQ ID NO: 5. Therefore, the invention also provides a monoclonal antibody which comprises (a) a heavy chain directed against the virulence antigen of *Y. pestis* encoded by the nucleic acid sequence of SEQ ID NO: 4, and (b) a light chain directed against the virulence antigen of *Y. pestis* encoded by the nucleic acid sequence of SEQ ID NO: 5. In addition, the invention provides a hybridoma cell line that produces such a monoclonal antibody.

While the nucleic acid sequence of the inventive gene transfer vector preferably encodes a wild-type monoclonal antibody directed against *Y. pestis*, the nucleic acid sequence can encode a mutant form of the monoclonal antibody. For example, the nucleic acid sequence can encode a mutant form of a heavy chain and/or light chain with altered (e.g., improved) effector function. Such mutants can be isolated or synthetically generated using methods known in the art and described herein. Antibody affinity also can be optimized using phage display techniques (see, e.g., Sidhu et al., *Methods Enzymol.*, 328: 333-363 (2000)) or computational protein design (see, e.g., Clark et al., *Protein Science*, 15: 949-960 (2006), and Lippow et al., *Nat. Biotechnol.*, 25(10): 1171-1176 (2007)).

Monoclonal antibodies may be obtained using a variety of techniques known to those skilled in the art, including standard hybridoma technology (see, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), supra). Monoclonal antibodies directed against virulence antigen of *Y. pestis* also are disclosed in, for example, Hill et al., *Infect. Immun.*, 65(11): 4476-4482 (1997), and Sofer-Podesta et al., *Molecular Therapy*, 16 (Suppl. 1): S268 (2008). Nucleic acid sequences encoding monoclonal antibodies can be isolated from corresponding hybridoma cell lines using RT-PCR and Rapid Amplification of cDNA Ends (RACE), or generated by total synthesis of the coding sequence with PCR.

The expression of the nucleic acid sequence in the inventive gene transfer vector is controlled by a suitable expression control sequence operably linked to the nucleic acid sequence. An "expression control sequence" is any nucleic acid sequence that promotes, enhances, or controls expression (typically and preferably transcription) of another nucleic acid sequence. Suitable expression control sequences include constitutive promoters, inducible promoters, repressible promoters, and enhancers. The nucleic acid sequence can be regulated by its endogenous promoter or by a normative promoter sequence. Examples of suitable normative promoters include the cytomegalovirus (CMV) immediate early (IE) promoter, the phosphoglycerate kinase (PGK) promoter, the long terminal repeat promoter of the Rous sarcoma virus (LTR-RSV), the sheep metallothionien promoter, and the human ubiquitin C promoter. The expression of the nucleic acid sequence in the inventive gene transfer vector is preferably regulated by the CMV IE promoter. Other preferred expression control sequences include the chicken β-actin promoter, the LTR-RSV promoter, the dendritic cell-specific dectin 2 promoter, and a chimeric expression control sequence comprising the CMV IE enhancer region and the chicken β-actin promoter. Suitable expression control sequences can be determined using eukaryotic expression systems such as are generally described in Sambrook et al., supra, and by using reporter gene systems (see, e.g., Taira et al., *Gene*, 263, 285-292 (2001)).

Preferably, the nucleic acid sequence in the inventive gene transfer vector further comprises a transcription-terminating region such as a polyadenylation sequence located 3' of the nucleic acid sequence. Any suitable polyadenylation sequence can be used, including a synthetic polyadenylation sequence, as well as the polyadenylation sequence of BGH (Bovine Growth Hormone), polyoma virus, SV40 (Human Sarcoma Virus-40), TK (Thymidine Kinase), EBV (Epstein Barr Virus), and the papillomaviruses, including human papillomaviruses and BPV (Bovine Papilloma Virus).

As set forth above, the inventive gene transfer vector preferably comprises at least one, but can comprise more than one, nucleic acid sequence (either encoding an immunogenic portion of a *Y. pestis* protein or a monoclonal antibody directed against *Y. pestis*). For example, the gene transfer vector can comprise 1, 2, 3, 4, 5, or more nucleic acid sequences, each of which encodes a different immunogenic portion of a *Y. pestis* protein or monoclonal antibody directed against *Y. pestis*. For example, the gene transfer vector can comprise multiple nucleic acid sequences, each of which encodes a heavy and/or light chain of a different monoclonal antibody. In addition, the gene transfer vector can comprise (a) a nucleic acid sequence which encodes an immunogenic portion of one or more proteins of *Yersinia pestis* and a heterologous signal peptide, and (b) a nucleic acid sequence which encodes a monoclonal antibody directed against *Yersinia pestis*, as described herein. It will be appreciated that multiple coding sequences can be expressed from a single gene transfer vector using any suitable method known in the art, such as employing a dual promoter cassette, separating coding sequences with a self-cleaving sequence (e.g., a 2A peptide from foot-and-mouth disease virus), or separating coding sequences with an internal ribosomal entry site (IRES).

When the inventive gene transfer vector comprises a nucleic acid sequence encoding an immunogenic portion of a *Y. pestis* protein, the nucleic acid sequence preferably further comprises a heterologous signal peptide. The term "signal peptide," as used herein, refers to a peptide, typically located at the amino terminus of a protein, which targets the protein to specific cellular compartments, such as the endoplasmic reticulum, and directs secretion of the mature protein from the cell in which it is produced. Signal peptides typically are removed from a precursor polypeptide and, thus, are not present in mature proteins. The signal peptide is "heterologous" in that either is not obtained or derived from a naturally occurring signal peptide of *Y. pestis*. The nucleic acid sequence that encodes a heterologous signal peptide can be naturally found in *Y. pestis*, but located at a normative position with respect to the immunogenic portion of the protein of *Y. pestis*.

One of ordinary skill in the art will appreciate that the presence of a heterologous signal peptide in the protein encoded by the inventive nucleic acid sequence mediates translocation of the polypeptide or protein to the endoplasmic reticulum, from which the protein is secreted from the cell. Any signal peptide that directs secretion of the protein encoded by the nucleic acid sequence is suitable for use in the inventive gene transfer vector. The heterologous signal peptide is preferably an immunoglobulin kappa (Igκ) signal peptide. The Igκ signal peptide can be obtained or derived from a mouse or a human. The nucleic acid sequence in the inventive gene transfer vector desirably is constructed such that, when expressed, the heterologous signal peptide is located at the N-terminus of the protein encoded by the nucleic acid sequence. In addition to signal peptides, other mechanisms for secretion may be employed, such as, for example, truncation, deletion, or point mutation of secretion-inhibiting sequences present in the nucleic acid sequence.

In accordance with the invention, the nucleic acid sequence which encodes at least an immunogenic portion of one or more proteins of *Yersinia pestis* comprises codons expressed more frequently in humans than in *Yersinia pestis*. While the genetic code is generally universal across species, the choice among synonymous codons is often species-dependent. Infrequent usage of a particular codon by an organism likely reflects a low level of the corresponding transfer RNA (tRNA) in the organism. Thus, introduction of a nucleic acid sequence into an organism which comprises codons that are not frequently utilized in the organism may result in limited expression of the nucleic acid sequence. One of ordinary skill in the art would appreciate that, to achieve maximum protection against *Y. pestis* infection, the inventive gene transfer vector must be capable of expressing high levels of *Y. pestis* proteins in a human host. In this respect, the inventive nucleic acid sequence encodes the native amino acid sequence of the immunogenic portion of the one or more *Y. pestis* proteins, but comprises codons that are expressed more frequently in humans than in *Y. pestis*. Such modified nucleic acid sequences are commonly described in the art as "humanized" or as utilizing "human-preferred" codons.

Thus, in the context of the invention, a *Y. pestis* nucleic acid sequence is said to be "humanized" if at least about 60% (e.g., at least about 70%, at least about 80%, or at least about 90%) of the wild-type codons in the nucleic acid sequence are modified to encode human-preferred codons. That is, a *Y. pestis* nucleic acid sequence is humanized if at least about 60% (e.g., at least about 70%, at least about 80%, or at least about 90%) of the codons encoded therein are human-preferred codons. A preferred humanized nucleic acid sequence encoding *Y. pestis* V antigen is set forth in SEQ ID NO: 6. However, the invention is not limited to this exemplary sequence. Indeed, genetic sequences can vary between different strains, and this natural scope of allelic variation is included within the scope of the invention. Additionally and alternatively, the humanized nucleic acid sequence encoding *Y. pestis* V antigen can be any sequence that has at least 80% (e.g., at least about 90%, at least about 95%, or at least about 98%) identity to SEQ ID NO: 6, or any sequence that hybridizes to SEQ ID NO: 6 under at least moderate, preferably high, stringency conditions, such as those described herein. Determining the degree of homology can be accomplished using any suitable method (e.g., BLASTnr, provided by GenBank).

Desirably, the inventive gene transfer vector is part of a pharmaceutical composition suitable for administration to a mammalian (e.g., human) host. In the context of the invention, the pharmaceutical composition can comprise a pharmaceutically acceptable carrier and a gene transfer vector comprising a nucleic acid sequence encoding an immunogenic portion of one or more proteins of *Yersinia pestis*, or a gene transfer vector comprising a nucleic acid sequence encoding a monoclonal antibody directed against *Y. pestis*, as described herein. Any suitable pharmaceutically acceptable carrier can be used within the context of the invention, and such carriers are well known in the art. The choice of carrier will be determined, in part, by the particular site to which the pharmaceutical composition is to be administered and the particular method used to administer the pharmaceutical composition. The following formulations are merely exemplary and are in no way limiting. However, oral, injectable, and aerosol formulations are preferred.

Formulations suitable for oral administration can consist of (a) liquid solutions, such as an effective amount of the gene transfer vector dissolved in diluents, such as water, saline, or orange juice, (b) capsules, sachets or tablets, each containing a predetermined amount of the gene transfer vector, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the gene transfer vector in a flavor, usually sucrose and acacia or tragacanth, as well as pastilles comprising the gene transfer vector in an inert base, such as gelatin and glycerin, or sucrose and acacia, emulsions, gels, and the like containing, in addition to the gene transfer vector, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for aerosol administration comprise the inventive gene transfer vector, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressurized preparations, such as in a nebulizer or an atomizer.

Other suitable formulations are possible, for example, suppositories can be prepared by use of a variety of bases such as emulsifying bases or water-soluble bases. Formulations suitable for vaginal administration can be presented as pessaries, tampons, creams, gels, pastes, foams, or spray formulas containing, in addition to the gene transfer vector, such carriers as are known in the art to be appropriate.

More preferably, the pharmaceutical composition is formulated to protect the gene transfer vector from damage prior to administration. For example, in embodiments where the gene transfer vector is an adenoviral vector, the particular formulation desirably decreases the light sensitivity and/or temperature sensitivity of the adenoviral vector. Indeed, the pharmaceutical composition will be maintained for various periods of time and, therefore, should be formulated to ensure stability and maximal activity at the time of administration. Typically, the pharmaceutical composition is maintained at a temperature above 0° C., preferably at 4° C. or higher (e.g., 4-10° C.). In some embodiments, it is desirable to maintain the pharmaceutical composition at a temperature of 10° C. or higher (e.g., 10-20° C.), 20° C. or higher (e.g., 20-25° C.), or even 30° C. or higher (e.g., 30-40° C.). The pharmaceutical composition can be maintained at the aforementioned temperature(s) for at least 1 day (e.g., 7 days (1 week) or more), though typically the time period will be longer, such as at least 3, 4, 5, or 6 weeks, or even longer, such as at least 10, 11, or 12 weeks, prior to administration to a patient. During that time period, the adenoviral gene transfer vector optimally loses no, or substantially no, activity, although some loss of activity is acceptable, especially with relatively higher storage temperatures and/or relatively longer storage times. Preferably, the activity of the adenoviral vector composition decreases about 20% or less, preferably about 10% or less, and more preferably about 5% or less, after any of the aforementioned time periods.

To this end, the pharmaceutical composition preferably comprises a pharmaceutically acceptable liquid carrier, such as, for example, those described above, and a stabilizing agent selected from the group consisting of polysorbate 80, L-arginine, polyvinylpyrrolidone, α-D-glucopyranosyl α-D-glucopyranoside dihydrate (commonly known as trehalose), and combinations thereof. More preferably, the stabilizing agent is trehalose, or trehalose in combination with polysorbate 80. The stabilizing agent can be present in any suitable concentration in the pharmaceutical composition. When the stabilizing agent is trehalose, the trehalose desirably is present in a concentration of about 2-10% (wt./vol.), preferably about 4-6% (wt./vol.) of the pharmaceutical composition. When trehalose and polysorbate 80 are present in the pharmaceutical composition, the trehalose preferably is present in a concentration of about 4-6% (wt./vol.), more preferably about 5% (wt./vol.), while the polysorbate 80 desirably is present in a concentration of about 0.001-0.01% (wt./vol.), more preferably about 0.0025% (wt./vol.). When a stabilizing agent, e.g., trehalose, is included in the pharmaceutical composition, the pharmaceutically acceptable liquid carrier preferably contains a saccharide other than trehalose. Suitable formulations of the pharmaceutical composition are further described in U.S. Pat. Nos. 6,225,289 and 6,514,943, and International Patent Application WO 00/34444.

When the inventive gene transfer vector is an adenoviral vector, the pharmaceutical composition can further be formulated to reduce adherence loss of the adenoviral vector on devices used to prepare, store, or administer the adenoviral vector, such as glassware, syringes, or needles. Use of such a pharmaceutical composition will extend the shelf life of the pharmaceutical composition, facilitate administration, and increase the efficacy of the inventive method. In this regard, the pharmaceutical composition also can be formulated to enhance the spread of the adenoviral vector throughout the target tissue and/or enhance transduction efficiency. To this end, the pharmaceutical composition also can comprise hyaluronidase, which has been shown to enhance uptake of adenoviral vectors. Addition of proteases to the pharmaceutical composition can enhance the spread of the adenoviral vector throughout the target tissue. The adenoviral vectors of the pharmaceutical composition can be bound to biocompatible solid carriers, such as particulate carriers (e.g., beads, wafers, etc.), that remain in the target tissue due to size, or incorporated into a matrix, such as gel or foam.

In addition, the pharmaceutical composition can comprise additional therapeutic or biologically-active agents. For example, therapeutic factors useful in the treatment of a particular indication can be present. Factors that control inflammation, such as ibuprofen or steroids, can be part of the pharmaceutical composition to reduce swelling and inflammation associated with in vivo administration of the gene transfer vector and physiological distress. Immune system suppressors can be administered with the pharmaceutical composition to reduce any immune response to the gene transfer vector itself. Alternatively, immune enhancers can be included in the pharmaceutical composition to upregulate the body's natural defenses against disease. Moreover, cytokines can be administered with the pharmaceutical composition to attract immune effector cells to the infection site.

The invention further provides a method of producing an immune response against *Yersinia pestis* in a host. The inventive method comprises administering to the host a gene transfer vector having a nucleic acid sequence which encodes at least an immunogenic portion of one or more proteins of *Y. pestis* and a heterologous signal peptide. The invention provides another method of producing an immune response against *Yersinia pestis* in a mammal. The method comprises administering to the mammal a gene transfer vector comprising a nucleic acid sequence which encodes a monoclonal antibody directed against *Yersinia pestis*. Preferably, the nucleic acid sequence encodes a monoclonal antibody directed against the virulence (V) antigen of *Y. pestis*. The inventive method desirably produces maximum levels of protective immunity against *Y. pestis* infection within a short time period, while minimizing or eliminating the need for repeat administrations to maintain immunity. In particular, when the gene transfer vector comprises a nucleic acid sequence encoding one or more proteins of *Y. pestis*, the inventive method desirably produces a cell-mediated immune response and/or a humoral immune response. When the gene transfer vector comprises a nucleic acid sequence encoding a monoclonal antibody directed against *Y. pestis*, the inventive method desirably produces a humoral immune response. Descriptions of the gene transfer vector, the nucleic acid sequence, the monoclonal antibody, the pharmaceutical composition, and components thereof set forth above in connection with the inventive gene transfer vector also are applicable to those same aspects of the aforesaid inventive method.

The inventive method is desirably performed in vivo, preferably within a mammal, and most preferably within a human. In some embodiments, however, ex vivo methods may be appropriate. When the method is performed in vivo, the invention provides a method of administering (i.e., inoculating or immunizing) the inventive gene transfer to a host, most preferably a human host. In accordance with the method, the gene transfer vector, such as is set forth above, is introduced into the host under conditions sufficient for the host to mount an immune response against the immunogenic portion of the one or more proteins of *Y. pestis*. While many methods of administration are known in the art, oral administration, intramuscular injection, and subdermal (i.e., subcutaneous) injection are preferred.

In some embodiments, it may be desirable to administer the gene transfer vector to antigen presenting cells of the host. In this respect, the gene transfer vector can be administered to dendritic cells of the host. As described above in connection with the inventive gene transfer vector, the gene transfer vector can be manipulated to ablate the natural tropism of the gene transfer vector, and introduce a new tropism for antigen presenting cells. The methods for modifying gene transfer vectors, particularly the coat proteins of adenoviral vectors, to preferentially bind dendritic cells are described above and are applicable to this embodiment of the inventive method.

The dose of the inventive gene transfer vector administered to a mammal, particularly a human, in the context of the invention will vary with the particular gene transfer vector, the composition containing the gene transfer vector, the method of administration, and the particular site being treated. The dose should be sufficient to affect a desirable response, preferably a humoral and/or a cell-mediated immune response against *Y. pestis* infection, within a desirable time frame. When the inventive gene transfer vector is an adenoviral vector, typical doses will contain at least about $1 \times 10^5$ particle units (pu) of the adenoviral vector (e.g., at least about $1 \times 10^6$ pu), preferably at least about $1 \times 10^7$ pu (e.g., at least about $1 \times 10^8$ pu). Higher doses also can be used, such as doses of at least about $1 \times 10^9$ pu (e.g., at least about $1 \times 10^1$ pu), or even at least about $1 \times 10^{11}$ pu (e.g., at least about $1 \times 10^{12}$ pu), or even higher, such as at least about $1 \times 10^{13}$ pu (e.g., at least about $1 \times 10^{14}$ pu). Generally, dosages will be about $1 \times 10^5$-$1 \times 10^{14}$ pu (e.g., about $1 \times 10^7$-$1 \times 10^{13}$ pu), preferably $1 \times 10^8$-$1 \times 10^{12}$ pu (e.g., about $1 \times 10^9$-$1 \times 10^{11}$ pu).

With respect to the number of administrations of the inventive gene transfer vector, the most preferred dosing schedule involves a single administration of a dose of the gene transfer vector to the host. However, if a single administration of the inventive gene transfer vector does not elicit a sufficient immune response against *Y. pestis* infection, a second dose can be administered to the host. In this regard, the inventive method can represent one arm of a prime and boost immunization regimen. The inventive method, therefore, can comprise administering to the mammal a priming composition(s) or a boosting composition(s). When a priming composition is administered to the mammal, the gene transfer vector is administered to the mammal after administration of the priming composition. When a boosting composition is administered to the mammal, the gene transfer vector is administered prior to administration of the boosting composition. In either case, the priming composition or the boosting composition(s) can comprise a second gene transfer vector comprising a nucleic acid sequence encoding at least one protein of *Y. pestis* or a *Y. pestis* antigen itself (e.g., an antigenic protein, intact pathogen inactivated pathogen, and the like).

In some embodiments, it may be desirable to administer multiple different gene transfer vectors to a mammal. For example, in order to maximize the protective immunity against *Y. pestis*, the inventive method can comprise administering multiple gene transfer vectors, each of which encodes an immunogenic portion of a different *Y. pestis* protein, or a different monoclonal antibody directed against *Y. pestis*.

The inventive method can be performed in combination with other methods for the prophylaxis or treatment of *Y. pestis* infection. In one embodiment, the inventive gene transfer vector can be administered before, after, or concurrently with antibiotics approved for use in managing *Y. pestis* infection. Such antibiotics include streptomycin, chloramphenicol, tetracycline, fluoroquinolones (e.g., ciprofloxacin), doxycycline, and gentamicin (see, e.g., Wagle, *Indian J. Med. Sci.*, 2: 489-494 (1948), Meyer, *JAMA*, 144: 982-985 (1950), Kilonzo et al., *Acta Tropica*, 50: 323-329 (1992), and Mwengee et al., *Clin. Infect. Dis.*, 42: 614-621 (2006)). In addition, the inventive method can be performed in combination with other methods for immunizing against *Y. pestis* infections, such as vaccination with live-attenuated vaccines, inactivated vaccines, or subunit vaccines.

The following examples further illustrate the invention but, of course, should not be construed as in any way limiting its scope.

Example 1

This example demonstrates a method for generating a gene transfer vector comprising a nucleic acid sequence encoding an immunogenic portion of the virulence antigen (V) of *Y. pestis*.

The *Y. pestis* V antigen gene (NCBI Accession No. B33601) with mammalian-preferred codons was synthesized by overlap polymerase chain reaction and fused to the human Igκ signal peptide for extracellular secretion. The V antigen gene was cloned into an E1A/E1B/E3-deficient adenoviral vector based on serotype 5, to generate AdsecV. AdNull was used as control vector with an identical vector backbone but no transgene (see, e.g., Hersh et al., *Gene Ther.*, 2: 124-131 (1995)). The adenoviral vectors were produced in 293 cells and were purified by double CsCl gradient centrifugation (see, e.g., Rosenfeld et al., *Cell*, 68: 143-155 (1992)).

Expression of the V antigen by AdsecV was assessed in vitro. In particular, the A549 lung epithelial cell line (American Type Culture Collection Deposit No. CCL185) was maintained in complete Dulbecco's modified essential medium. Cells were infected with AdsecV or AdNull (500 particle units (pu)/cell) in low-serum medium. 24 hours after infection, cells and medium were collected, and proteins were separated by SDS-PAGE (Invitrogen, Carlsbad, Calif.) and transferred to polyvinylidene fluoride membrane (BioRad Laboratories, Hercules, Calif.). For Western blot analysis, the membrane was probed with a 1:1000 dilution of a rabbit anti-V antigen antibody. A peroxidase-conjugated anti-rabbit antibody (Santa Cruz Biotechnology, Santa Cruz, Calif.) and a chemiluminescent peroxidase substrate (ECL+reagent; Amersham Biosciences, Piscataway, N.J.) were used for detection.

To assess V antigen expression by immunofluorescence, 24 hours after infection cells were fixed with 4% paraformaldehyde and blocked with 5% goat serum (Jackson Immuno-Labs, West Grove, Pa.), 1% bovine serum albumin in PBS with 0.05% saponin (Sigma-Aldrich, St. Louis, Mo.), and 0.1% Triton X-100 (Sigma-Aldrich, St. Louis, Mo.), followed by incubation with the rabbit anti-V antigen antibody diluted 1:1000. A goat anti-rabbit secondary antibody conjugated to Al-exa 488 fluorophore (Jackson ImmunoLabs, West Grove, Pa.) was used at a final concentration of 10 μg/mL. Nuclei were counterstained with 4',6-diamidino-2-phenylindole (Molecular Probes). The samples were observed by fluorescence microscopy with an Olympus IX70 inverted microscope (New York/New Jersey Scientific) equipped with a X60 PlanApo NA 1.4 objective, and digital image analysis was performed with Metamorph imaging software (version 4.6r9; Molecular Devices, Sunnyvale, Calif.)

Twenty four hours after infection of A549 cells with AdsecV, a protein with the expected size for V antigen (37 kDa) was identified in medium and cell lysates. The V antigen was not detected in cells infected with AdNull or in uninfected cells. At 24 hours, the V antigen in the AdsecV-infected cells exhibited a broad, diffuse staining pattern as well as a bright, punctuate, perinuclear staining pattern consistent with localization of V antigen in the endoplasmic reticulum and Golgi apparatus of the secretory pathway.

This example demonstrates the generation of an adenoviral vector comprising a nucleic acid sequence encoding the *Y. pestis* V antigen, and expression of V antigen therefrom in vitro.

Example 2

This example demonstrates a method of inducing an immune response in a mammal comprising administering a gene transfer vector comprising a nucleic acid sequence encoding a *Y. pestis* protein.

Female BALB/c mice were obtained from Taconic (Hudson, N.Y.). Mice were housed under specific pathogen-free conditions and were used at 7 weeks of age. Mice were immunized in a single vaccination by two intramuscular injections with 50 μL of the AdsecV preparation described in Example 1, which was divided evenly between the quadriceps on each side. Adenoviral vectors were diluted with saline to the specified dose.

To assess transgene-specific humoral immune responses, serum samples from immunized mice were obtained from the tail vein, and anti-V antigen serum antibody titers were determined by ELISA. For vector dose response, serum samples were obtained from mice 4 weeks after immunization with AdsecV at doses ranging from $10^8$ to $10^{11}$ pu. For time-dependent anti-V antigen antibody titers, mice were immunized with a single administration of $10^9$ pu of AdsecV, and serum samples were obtained before and at 1, 2, 4, 6, and 8 weeks after vaccination. For IgG subtypes, mice were vaccinated with $10^9$ pu of AdsecV, and serum samples were obtained 5 weeks after immunization.

For ELISAs, microtiter plates (Corning, Corning, N.Y.) were coated with 0.5 μg of recombinant V antigen per well. After blocking, serum samples were added in sequential 2-fold dilutions starting at 1:20 and were incubated for 1 hour at 23° C. An anti-mouse IgG-horseradish peroxidase conjugate (Sigma-Aldrich, St. Louis, Mo.) was used at 1:10,000 dilution. Detection was accomplished using a peroxidase substrate (BioRad Laboratories, Hercules, Calif.). Absorbance at 415 nm was read using a microplate reader (BioRad Laboratories, Hercules, Calif.). Class-specific anti-IgG antibodies (IgG1, IgG2a, IgG2gb, and IgG3) were determined using the Mouse Typer isotyping panel (BioRad Laboratories, Hercules, Calif.). Antibody titers were calculated on the basis of a log(optical density)–log(dilution) interpolation model and a cutoff value equal to 2-fold the absorbance of the background (Plikaytis et al., *J. Clin. Microbiol.*, 29: 1439-1446 (1991), and Price et al., *Infect. Immun.*, 69: 4509-4515 (2001)).

Four weeks after the single intramuscular administration of $10^8$ to $10^{11}$ pu of AdsecV, a dose response in the total anti-V antigen IgG titers was observed, with the total anti-V antigen IgG titers for immunized mice reaching a mean±SE titer of 76,000±16,000 for the mice vaccinated with $10^{11}$ pu of AdsecV. No anti-V antigen IgG titers were detected in the naïve mice (which received saline) or in the AdNull-immunized mice.

After administration of a $10^9$ pu dose of AdsecV, anti-V antigen titers were detected in serum of immunized mice as early as 1 week. The antibody titer reached a maximum level at 2 weeks and remained high through 8 weeks. Analysis of IgG subclasses at the $10^9$ pu AdsecV dose showed a strong response for both IgG1 and IgG2a and a lesser response for IgG2b and IgG3. Similar antibody titers and subtypes were observed with an adenoviral vector expressing a nonsecreted form of V antigen. Anti-V antigen antibody after immunization with $10^9$ pu of the nonsecreted form could be detected in serum at 2 weeks, with a mean±SE titer of 13,700±2,900. Antibody levels remained high through week 8.

This example demonstrates a method of inducing a humoral immune response in a mammal using an adenoviral vector encoding the V antigen of *Y. pestis*.

Example 3

This example demonstrates a method of inducing an immune response in a mammal comprising administering a gene transfer vector comprising a nucleic acid sequence encoding a *Y. pestis* protein.

To assess transgene-specific cell-mediated immune responses, female BALB/c mice as described above were immunized intramuscularly (n=5) with either saline, AdNull ($10^{11}$ pu), or AdsecV ($10^{11}$ pu). The frequency of antigen-specific T lymphocytes was determined using an interleukin-2 (IL-2)-, interferon gamma (IFN-γ)-, and IL-4-specific enzyme linked immunospot (ELISPOT) assay (R&D Systems, Minneapolis, Minn.). Six days after administration of the adenoviral vectors, CD4+ or CD8+ T cells were purified by negative depletion using SpinSep T cell subset purification kits (StemCell Technologies, Vancouver, BC, Canada). Splenic dendritic cells (DCs) were purified from naïve mice by positive selection using CD11cMACS beads (Miltenyi Biotec, Bergisch Gladbach, Germany) and double purification over 2 MACS-LS columns (Miltenyi Biotec, Bergisch Gladbach, Germany). The purity of CD4+ T cells, CD8+ T cells, and DCs was assessed by staining with anti-CD4-phycoerythrin (PE), anti-CD8-PE, and anti-CD11c-PE antibodies (BD Biosciences, Franklin Lakes, N.J.), respectively. Cell purity evaluation and cell counts were performed using a FACScalibur flow cytometer running at a constant flow rate. For ELISPOT assays, $10^5$ CD4+ or CD8+ T cells were incubated for 36 hours with splenic DCs at a ration of 4:1, with or without purified V antigen. Spots were counted by computer-assisted ELISPOT image analysis (Zellnet Consulting, Fort Lee, N.J.).

V antigen-specific IL-2 secretion (mean±SE, 52±6 spots/$10^5$ CD4+ T cells) as well as IFN-γ secretion (mean±SE, 91±3 spots/$10^5$ CD4+ T cells) was significantly higher ($p<0.005$ and p<0.0001, respectively) in CD4+ T cells from the AdsecV-immunized mice than in the two control groups. In contrast, no significant differences were observed for V antigen-specific IL-4 production. CD8+ T cell activation was evaluated by V antigen-specific IL-2 and IFN-γ secretion. Both IL-2 (mean±SE, 19±4 spots/05 CD8+ T cells) and IFN-γ (mean±SE, 24±3 spots/$10^5$ CD8+ T cells) responses were higher in the AdsecV-vaccinated mice than in the two control groups (p<0.005). The naïve mice and the mice immunized with AdNull showed no significant signal of V antigen-induced cytokine production above background.

This example demonstrates a method of inducing a cell-mediated immune response in a mammal using an adenoviral vector encoding the V antigen of *Y. pestis*.

Example 4

This example demonstrates that administration of a gene transfer vector comprising a nucleic acid sequence encoding a *Y. pestis* protein to a mammal protects the mammal from infection by *Y. pestis*.

*Y. pestis* challenge studies were conducted under biosafety level 3 conditions. Four weeks or 6 months after immunization, BALB/c mice (10/group) were challenged intranasally with *Y. pestis* C092. *Y. pestis* C092 was grown aerobically in heart infusion broth (Difco, Lawrence, Kans.) at 30° C. and was diluted in saline solution at doses ranging from $10^3$ to $10^6$ cfu. Fifty microliters of bacterial suspension was used for intranasal infection of mice. Bacterial dose was controlled by plating on *Yersinia* selective agar (YSA; Oxoid, Hampshire, UK). Survival was monitored daily for 15 days. From a subset of the mice that died after challenge, liver, spleen, and lungs were removed, homogenized in saline solution, and plated on YSA, to confirm that plague was the cause of death. A subset of the vaccinated mice that survived the challenge were killed 15 days after infection; liver, spleen, and lungs were removed, homogenized in saline solution, and plated on YSA to confirm that bacteria were not present in internal organs.

To evaluate the protective capacity of the AdsecV vaccine at different challenge doses, mice were infected intranasally with $10^3$ to $10^6$ cfu of *Y. pestis* C092 4 weeks after a single administration of $10^{11}$ pu of AdsecV. Mice were protected at all doses. All AdsecV-immunized mice (10/10) survived the challenge with $10^3$ (p<0.005) and $10^4$ (p<0.0001) cfu, whereas the naïve mice and the mice immunized with $10^{11}$ pu of AdNull died within 3-5 days. At higher challenge doses, 80% (8/10) and 90% (9/10) of the mice survived after intranasal infection with $10^5$ and $10^6$ cfu of *Y. pestis* C092, respectively (p<0.0001).

The capacity of the AdsecV vaccine to confer long-term protection was evaluated by challenge at 6 months after immunization with $10^{11}$ pu of AdsecV. Anti-V antigen total IgG titers in immunized mouse serum before challenge were a mean±SE of 106,00±16,500 (n=20). Mice were infected intranasally with $10^4$ or $10^6$ cfu of *Y. pestis* C092. All AdsecV-immunized mice (10/10) survived the challenge with $10^4$ cfu, and 90% (9/10) of the AdsecV-immunized mice survived the challenge with $10^6$ cfu and (p<0.0001, for both doses), whereas none of the 10 naïve mice survived the challenge with $10^4$ cfu *Y. pestis* C092.

This example demonstrates that immunization of a mammal with an adenoviral vector encoding the *Y. pestis* V antigen protects the mammal from *Y. pestis* infection.

Example 5

This example demonstrates a method of generating protective monoclonal antibodies directed against the Virulence (V) antigen of *Y. pestis*, as well as the use of a gene transfer vector encoding the heavy and light chains of such a monoclonal antibody.

To generate hybridomas, a mouse or other host animal is immunized with recombinant V antigen or a vector expressing V antigen by subcutaneous, intraperitoneal, or intramuscular routes to elicit B lymphocytes that secrete V antigen-specific antibodies. Spleens from immunized animals are isolated, reduced to a cell suspension, and fused with a myeloma cell line. These hybridomas are grown in a culture medium that contains selective agents that inhibit the growth of unfused cells. Culture medium from the hybridoma cells is assayed for production of antibodies reactive with V antigen. After identification of reactive cells, the clones are subcloned by limiting dilution. These hybridoma cells also can be grown as ascites tumors in animals.

The monoclonal antibodies secreted by the cloned hybridoma cells are extracted from culture medium, ascites fluid, or serum by standard protein purification methods. Monoclonal antibodies with protective characteristics against *Y. pestis* are identified in in vivo *Y. pestis* challenge experiments. For these experiments, purified antibodies, concentrated hybridoma cell supernatant, or ascites fluid is administered to mice. At two hours post-administration, the animals are challenged with a lethal dose of *Y. pestis* and survival is monitored.

A replication-defective adenoviral vector expressing a monoclonal antibody reactive with the *Y. pestis* V antigen and protective against *Y. pestis* challenge is produced. A series of monoclonal antibodies are screened for protective efficacy against *Y. pestis* challenge in an in vivo model. To obtain the antibody sequence corresponding to a protective antibody, RNA is extracted from a hybridoma cell line expressing the antibody, and the coding sequences are isolated by a combination of RT-PCR and RACE (rapid amplification of cDNA ends). The individual antibody heavy and light chains are cloned for sequence analysis.

After sequence confirmation, PCR is used to engineer the heavy and light chains for expression as a single polypeptide separated by a self-cleaving sequence. This modified coding sequence is cloned into a mammalian expression vector based on replication-defective human adenovirus serotype 5.

The replication-defective adenoviral vector co-expressing the heavy and light chains of a protective anti-V antigen monoclonal antibody is introduced into a mammalian host by direct administration. The coding sequence is expressed in transduced cells and results in antibody expression and protection against lethal challenge with the bacterium.

Example 6

This example demonstrates a method of inducing an immune response in a mammal comprising administering a gene transfer vector comprising a nucleic acid sequence encoding a monoclonal antibody directed against the V antigen of *Y. pestis*.

A panel of monoclonal antibodies against the *Y. pestis* V antigen was generated using hybridoma technology. Following intraperitoneal administration of concentrated hybridoma supernatants, one monoclonal antibody, 2C12.4, consistently protected mice against a lethal intranasal challenge with *Y. pestis*. The coding sequences for the heavy and light chains of this protective antibody were isolated from the corresponding hybridoma line and cloned into a replication-deficient serotype 5 human adenovirus vector to generate AdαV. Separation of the heavy and light chain subunits by the self-cleaving 2A peptide from foot-and-mouth disease virus facilitated expression of both protein subunits from a single CMV promoter.

Western blot analysis of AdαV-infected cell supernatants under denaturing and reducing conditions demonstrated the presence of both heavy and light chains. When these supernatants were analyzed using native (non-reducing) Western conditions, a protein of the expected size for a completely assembled monoclonal antibody was detected, and Western analysis demonstrated the specificity of AdαV-expressed antibody for V antigen. The time-dependent expression of the anti-V antigen antibody in serum was determined by a V antigen-specific ELISA following intravenous administration of AdαV to C57B1/6 mice. At various times post-AdαV administration, the serum levels of anti-V antigen antibodies were determined by ELISA.

As early as one day post-administration, high levels of anti-V antigen antibody titers were detectable ($43 \times 10^3 \pm 4 \times 10^3$). These titers peaked by day 3 post-administration ($90 \times 10^2 \pm 13 \times 10^3$) and remained detectable through a 12 week time course. No anti-V antigen antibody titers were detectable in either naïve mice or mice receiving control vectors. When animals that received AdαV were challenged with *Y. pestis* at day 4 post-administration, 80% of the animals were protected, while 100% of control animals died ($p<0.01$).

This example demonstrates that an adenoviral vector encoding a monoclonal antibody directed against V antigen of *Y. pestis* can induce a protective immune response against *Y. pestis* infection in a mammal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A monoclonal antibody which comprises (a) a heavy chain directed against the virulence antigen of *Y. pestis* encoded by the nucleic acid sequence of SEQ ID NO: 4, and (b) a light chain directed against the virulence antigen of *Y. pestis* encoded by the nucleic acid sequence of SEQ ID NO: 5.

2. A hybridoma cell line that produces the monoclonal antibody of claim 1.

* * * * *

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Cys Arg Gly Asp Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: "Xaa" may be any amino acid
<220> FEATURE:
<221> NAME/KEY: MISC_FEATURE
<222> LOCATION: (2)..(2)
<223> OTHER INFORMATION: "Xaa" may be any amino acid
<220> FEATURE:
<221> NAME/KEY: MISC_FEATURE
```

```
<222> LOCATION: (8)..(8)
<223> OTHER INFORMATION: "Xaa" may be any amino acid

<400> SEQUENCE: 2

Cys Xaa Cys Arg Gly Asp Cys Xaa Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Cys Asp Cys Arg Gly Asp Cys Phe Cys
1               5

<210> SEQ ID NO 4
<211> LENGTH: 1425
<212> TYPE: DNA
<213> ORGANISM: Artificial Sequence
<220> FEATURE:
<223> OTHER INFORMATION: Synthetic

<400> SEQUENCE: 4
atgggcaggc ttacttttc attcttgcta ctgattgtcc ctgcatatgt cctgtgccag      60
gtaactctga aagagtctgg ccctgggata ctgcagccct cccagaccct cagtctgact     120
tgttctttct ctgggttttc actgagcacc tctaatttgg gtgtaggctg gattcgtcag     180
tcttcaggga agggtctgga gtggctctta cacattttgt ggaatggtaa taagttctat     240
aacccagccc tgaagagccg gctcacaatc tccaaggata cctactccaa ccaggtattc     300
ctccagatcg ccaatgtgga cactgcggat actgccacat actactgtgc tcgaatcacg     360
ggtacgaact actttgacta ctggggccaa ggcaccactc tcacagtctc ctcagccaaa     420
acaacacccc catcagtcta tccactggcc ctgggtgtg agatacaac tggttcctcc      480 gtgactctgg gatgcctggt caagggctac ttccctgagt cagtgactgt gacttggaac     540
tctggatccc tgtccagcag tgtgcacacc ttcccagctc tcctgcagtc tggactctac     600
actatgagca gctcagtgac tgtcccctcc agcacctggc caagtcagac cgtcacctgc     660
agcgttgctc acccagccag cagcaccacg gtggacaaaa aacttgagcc cagcgggccc     720
atttcaacaa tcaaccctg tcctccatgc aaggagtgtc acaaatgccc agctcctaac     780
ctcgagggtg gaccatccgt cttcatcttc cctccaaata tcaaggatgt actcatgatc     840
tccctgacac ccaaggtcac gtgtgtggtg gtggatgtga gcgaggatga cccagacgtc     900
cagatcagct ggtttgtgaa caacgtggaa gtacacacag ctcagacaca aacccataga     960
gaggattaca acagtactat ccgggtggtc agcaccctcc ccatccagca ccaggactgg    1020
atgagtggca aggagttcaa atgcaaggtc aacaacaaag acctcccatc acccatcgag    1080
agaaccatct caaaaattaa agggctagtc agagctccac aagtatacat cttgccgcca    1140
ccagcagagc agttgtccag gaaagatgtc agtctcactt gcctggtcgt gggcttcaac    1200
cctggagaca tcagtgtgga gtggaccagc aatgggcata cagaggagaa ctacaaggac    1260
accgcaccag tcctggactc tgacggttct tacttcatat atagcaagct caatatgaaa    1320
acaagcaagt gggagaaaac agattccttc tcatgcaacg tgagcacga gggtctgaaa     1380 aattactacc tgaagaagac catctcccgg tctccgggta aatga                    1425
```

<210> SEQ ID NO 5
<211> LENGTH: 717
<212> TYPE: DNA
<213> ORGANISM: Artificial Sequence
<220> FEATURE:
<223> OTHER INFORMATION: Synthetic

<400> SEQUENCE: 5

| | |
|---|---|
| atggagacag acacactcct gctatgggtg ctgctgctct gggttccagg ttccactggt | 60 |
| gacattgtgc tgacacagtc gcctgcttcc ttgcctgttt ctctggggca gagggccacc | 120 |
| atctcatgca gggccagcca agtgtcggt acatctacct atagttatat acactggtac | 180 |
| caacagaaac caggacagcc acccaaactc ctcatgaagt atacatccaa cctagaatct | 240 |
| ggggtccctg ccaggttcag tggcagtggg tctgggacag acttcaccct caacatccat | 300 |
| cctgtggagg aggatgattc tgcaacatat tactgtcagc acagttggga gattccgttc | 360 |
| acgttcggag gggggaccaa gctggaagta aaacgggctg atgctgcacc aactgtatcc | 420 |
| atcttcccac catccagtga gcagttaaca tctggaggtg cctcagtcgt gtgcttcttg | 480 |
| aacaacttct accccaaaga catcaatgtc aagtggaaga ttgatggcag tgaacgacaa | 540 |
| aatggcgtcc tgaacagttg gactgatcag gacagcaaag acagcaccta gcatgagc | 600 |
| agcaccctca cgttgaccaa ggacgagtat gaacgacata cagctatac ctgtgaggcc | 660 |
| actcacaaga catcaacttc acccattgtc aagagcttca caggaatga gtgttag | 717 |

<210> SEQ ID NO 6
<211> LENGTH: 981
<212> TYPE: DNA
<213> ORGANISM: Artificial Sequence
<220> FEATURE:
<223> OTHER INFORMATION: Synthetic

<400> SEQUENCE: 6

| | |
|---|---|
| atgatccgcg cctacgaaca gaaccccag catttcatcg aagatctgga aaaggtgcgg | 60 |
| gtggaacagc tgaccggcca tggctcctcc gtgctcgaag aactggtcca gctcgtcaag | 120 |
| gataagaata tcgatatctc catcaagtat gatccccgca aggattccga ggtgttcgcc | 180 |
| aatcgcgtga tcaccgatga tatcgaactg ctcaagaaga tcctggccta tttcctgccc | 240 |
| gaggatgcca tcctgaaggg cggccattat gacaaccagc tgcagaatgg catcaagcgc | 300 |
| gtgaaggagt tcctggagtc ctcccccaat acccagtggg aactgcgggc cttcatggcc | 360 |
| gtgatgcatt tctccctgac cgccgatcgg atcgatgatg atatcctgaa ggtgatcgtc | 420 |
| gactccatga atcaccacgg cgatgcccgc agcaagctgc gcgaagaact cgccgagctc | 480 |
| accgccgaac tcaagatcta ttccgtcatc caggccgaaa tcaataagca tctgtccagc | 540 |
| agcggcacca tcaatatcca tgataagtcc atcaatctca tggataagaa tctctatggc | 600 |
| tataccgatg aagagatctt caaggccagc gccgagtaca agatcctcga aagatgccc | 660 |
| cagaccacca tccaggtgga tggcagcgag aagaagatcg tctccatcaa ggacttcctc | 720 |
| ggcagcgaga taagcgcac cggcgccctg ggcaatctga agaactccta ctcctataat | 780 |
| aaggataata atgaactgtc ccacttcgcc accacctgct ccgataagtc ccgccccctc | 840 |
| aacgacctgg tgagccagaa gaccacccag ctgtccgata tcaccagccg gttcaattcc | 900 |
| gccatcgaag ccctgaaccg gttcatccag aagtatgatt ccgtgatgca gcggctgctc | 960 |
| gatgacacct ccggcaagtg a | 981 |